United States Patent [19]
Brooks et al.

[11] Patent Number: 5,749,370
[45] Date of Patent: May 12, 1998

[54] METHOD AND SYSTEM FOR HOLDING THE POSITION OF A GUIDING MEMBER

[75] Inventors: Dennis L. Brooks, Santa Clara; Alfredo G. Bayot, Newark; Mina W. B. Chow, San Jose; Paul F. Muller, San Carlos, all of Calif.

[73] Assignee: Advanced Cardiovascular Systems, Inc., Santa Clara, Calif.

[21] Appl. No.: 483,478

[22] Filed: Jun. 7, 1995

Related U.S. Application Data

[63] Continuation-in-part of Ser. No. 324,010, Oct. 14, 1994, Pat. No. 5,558,101.

[51] Int. Cl.⁶ .................................................. A61B 5/00
[52] U.S. Cl. .................. 128/772; 128/657; 128/473; 128/434; 600/433; 600/434
[58] Field of Search .............................. 128/657, 658, 128/772; 604/95, 164, 280–283; 606/108

[56] References Cited

U.S. PATENT DOCUMENTS

| | | | |
|---|---|---|---|
| 5,318,527 | 6/1994 | Hyde et al. | 604/95 |
| 5,387,219 | 2/1995 | Rappe | 606/108 |
| 5,388,590 | 2/1995 | Horrigan et al. | 128/772 |

FOREIGN PATENT DOCUMENTS

| | | | |
|---|---|---|---|
| 0 415 332 A1 | 6/1991 | European Pat. Off. | |
| WO A 92 07608 | 5/1992 | WIPO | |

*Primary Examiner*—Sam Rimell
*Assistant Examiner*—Pamela L. Wingood
*Attorney, Agent, or Firm*—Heller, Ehrman, White & McAuliffe

[57] ABSTRACT

A method and system for maintaining the position of a guiding member, such as a guidewire, within a patient's vascular system, particularly within a guiding catheter disposed within the patient's vascular system, while an intravascular catheter slidably mounted on the guiding member is withdrawn and a replacement catheter is advanced over the guiding member. One presently preferred embodiment includes a guiding sheath having an inner lumen extending the length thereof with an engaging device slidably disposed with the guiding sheath. The guidewire engaging device is torqued from its proximal end which extends out of the proximal end of the guiding catheter so that the flexible distal end wraps around the guidewire tightly enough to maintain the position of the guidewire while withdrawing or advancing a catheter over the guidewire. The distal portion of the guidewire engaging device is preferably a pseudoelastic NiTi alloy which is in a stable austenite phase at body temperature (37° C.) and which exhibits a stress-induced transformation from the austenite phase to a martensite phase.

4 Claims, 3 Drawing Sheets

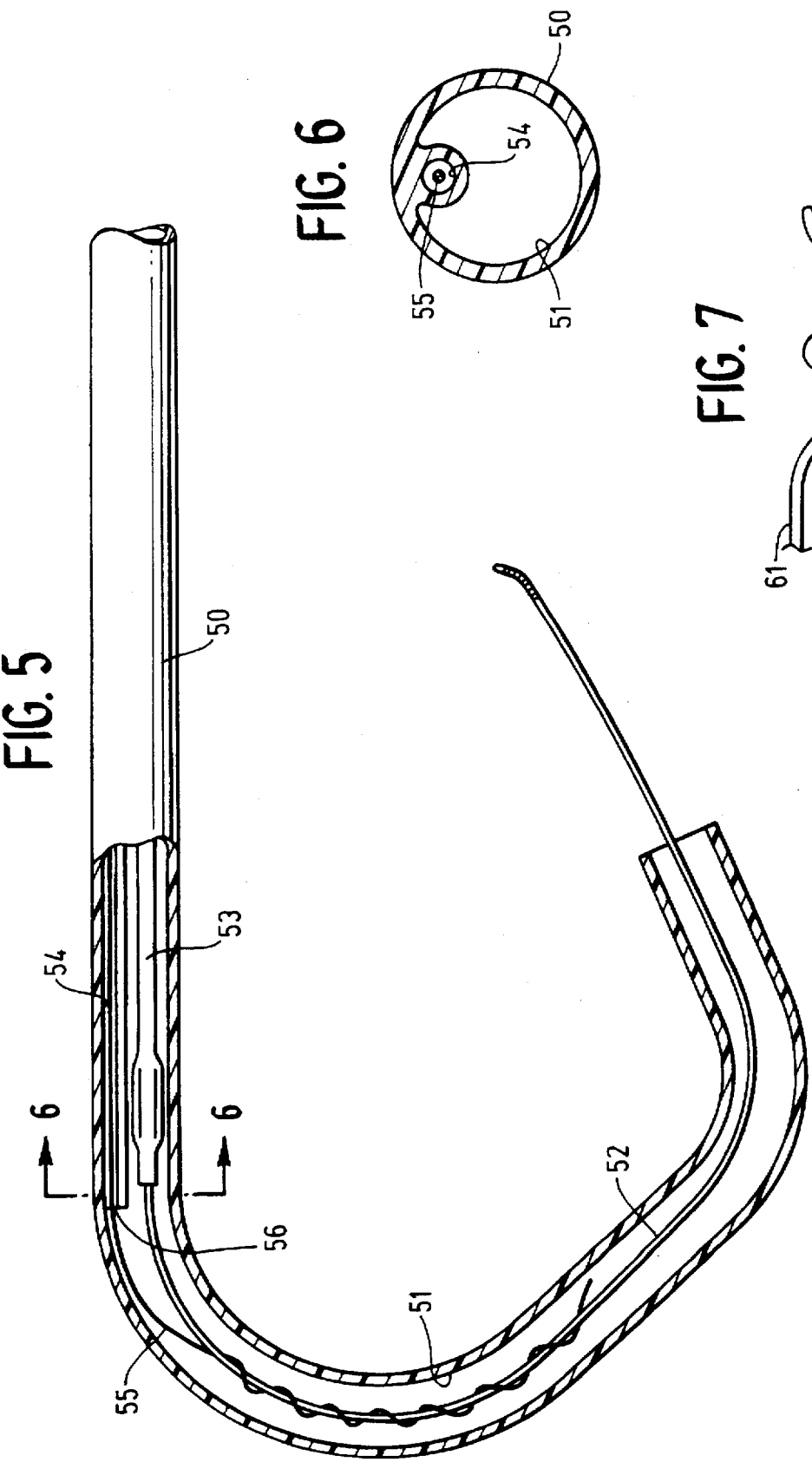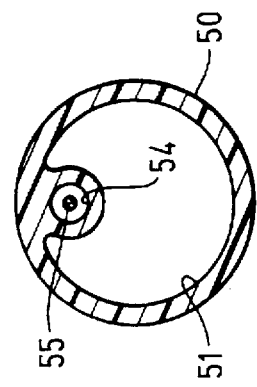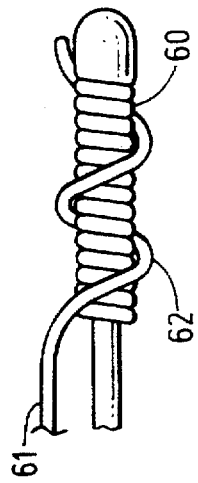

METHOD AND SYSTEM FOR HOLDING THE POSITION OF A GUIDING MEMBER

This application is a continuation-in-part of U.S. Pat. No. 5,558,101 (U.S. Ser. No. 08/324,010), filed Oct. 14, 1994, issued Sep. 24, 1996, the disclosure of which is incorporated by reference herein.

BACKGROUND OF THE INVENTION

This invention generally relates to the field of intravascular catheters which are advanceable over a guidewire into a desired region of a patient's vasculature, and particularly to dilatation, atherectomy catheters and the like which are advanceable into a patient's coronary arteries for therapeutic or diagnostic procedures therein.

In typical angioplasty procedures, a guiding catheter having a preshaped distal tip is percutaneously introduced by a Seldinger technique into the cardiovascular system of a patient and advanced within the system until the preshaped distal tip of the guiding catheter is disposed within the ascending aorta adjacent the ostium of the desired coronary artery. The guiding catheter is relatively stiff and when it is twisted or torqued from its proximal end, which extends outside the patient, the distal tip of the guiding catheter is guided into the desired coronary ostium. With the distal end of the guiding catheter well seated within the ostium of the desired coronary artery, a balloon dilatation catheter is introduced into and advanced through the guiding catheter and out the distal tip thereof into the patient's coronary artery until the balloon on the distal extremity of the dilatation catheter is properly positioned across the lesion to be dilated. Once properly positioned, the balloon is inflated one or more times to a predetermined size with radiopaque liquid at relatively high pressures (e.g., generally 4–12 atmospheres) to dilate the stenotic region of the diseased artery. When the dilatations have been completed, the balloon is finally deflated so that the dilatation catheter can be removed from the dilated stenosis to allow the resumption of normal blood flow through the dilated artery. The atherectomy procedures are similar except that the atheroma is severed from the arterial wall rather than the balloon expanding as in balloon angioplasty.

One frequently used type of angioplasty catheter is the over-the-wire type catheter which has an inner lumen extending within the catheter shaft which is configured to slidably receive a guidewire which facilitates advancement of the catheter over the guidewire to the desired location within the patient's coronary arteries. The guidewire receiving inner lumen may extend the entire length of the catheter as in conventional over-the-wire catheters or only in the distal portion of the catheter between a distal guidewire port and a proximal guidewire port which is spaced a short distance proximally from the distal guidewire port and a substantial distance from the proximal end of the catheter as in rapid exchange catheters.

It is not uncommon during an angioplasty procedure to exchange the dilatation catheter once the dilatation catheter has been advanced within the patient's arterial system. For example, if the physician determines that the inflated size of the balloon or the length of the balloon is inappropriate for the stenosis to be dilated, the dilatation catheter will be withdrawn and an appropriately sized dilatation catheter will be advanced into the coronary artery over the guidewire which remains in-place to dilate the stenosis. However, if the catheter is a conventional over-the-wire catheter, before the catheter is withdrawn either the guidewire in place must be replaced with an exchange wire, which is similar to the in-place guidewire except about twice as long, e.g. about 300 cm, as the normal guidewire or an extension wire about the same length as the in-place guidewire must be secured to the proximal end of the in-place guidewire to facilitate the withdrawal of the catheter without loss of the distal position of the guidewire. The reason it is important to maintain the position of the distal tip of the guidewire across the stenosis, is that if the guidewire is withdrawn, it may take the physician from about 15 minutes to about two hours or more to readvance a guidewire into the patient's coronary artery and across the stenosis to be dilated and then advance the balloon on the dilatation catheter across the stenotic region.

What has been needed and heretofore unavailable is a system for exchanging over-the-wire type and other types of intravascular catheters without the use of exchange wires or extension wires and which can hold the distal extremity of the guidewire in position within the distal end of the guiding catheter without occluding the passageway of the guiding catheter. The present invention satisfies these and other needs.

SUMMARY OF THE INVENTION

The present invention is directed to a system and method of using the system for holding a guiding member such as a guidewire in place within a patient's arterial system while an intravascular catheter is moved over the guiding member.

The system of the invention includes an elongated engaging device which has means on a distal extremity thereof for engaging a distal portion of a guiding member so as to maintain the position of the distal portion of the guiding member while an intravascular catheter is advanced or withdrawn over the guiding member.

In a presently preferred embodiment of the system, the elongated engaging device has a flexible shaped distal section which is configured to so as to wrap around and engage a distal portion of the guiding member when the engaging device is torqued from its proximal extremity. After several turns, e.g. about 3 to about 30, the flexible distal section will engage the in-place guiding member tightly enough to maintain the position of the guiding member when an intravascular catheter is moved over the guiding member. Preferably, the elongated engaging device is slidably disposed within an inner lumen of a guiding sheath which has an inner lumen extending the length thereof.

The engaging device is longer than the guiding sheath so that the flexible distal section of the member or other engaging means which engages the in-place guiding member will extend out the distal end of the guiding sheath and the proximal end of the guidewire engaging device which is torqued or other operating means will extend out the proximal end of the guiding sheath. The flexible distal section is preferably formed of a pseudoelastic NiTi alloy, such as described in copending applications Ser. No. 07/994,679 filed on Dec. 22, 1992 and Ser. No. 08/071,322 filed on Jun. 2, 1993 incorporated herein by reference, which is in a stable austenite phase at body temperature and which has pseudoelastic properties, i.e. stress induced transformation of the austenite phase to a martensite phase.

In the method of using the system, the guiding sheath is disposed in the patient's vasculature preferably within a guiding catheter with the elongated engaging device slidably disposed within the inner lumen of the guiding sheath. The intravascular catheter to be removed is pulled back into the inner lumen of the guiding catheter proximal to the distal end of the guiding sheath. With the distal portion of the engaging device extending out of the guiding sheath, but still within the guiding catheter, the proximal end of the engaging device, which extends out of the patient, is rotated or torqued causing the flexible distal section of the guidewire engaging device to wrap around an in-place guidewire within the guiding catheter tightly enough so as to maintain the position of the in-place guidewire when the catheter which is slidably mounted on the in-place guidewire is withdrawn or otherwise moved.

While the position of the in-place guiding member is being maintained by the engaging device, a replacement catheter may be mounted on the proximal end of the in-place guiding member, which extends out the proximal end of the guiding catheter, and then be advanced over the in-place guiding member to a location within the guiding catheter. To disengage the engaging device from the guiding member, the distal portion of the engaging device is unwrapped or loosened from the guiding member by rotating the proximal end of the engaging device in a direction opposite to the direction it was rotated to wrap around the distal portion of the guiding member. The engaging device is then pulled back into the guiding sheath and then both the guiding sheath and the disengaged engaging device may be withdrawn from the patient.

In an alternative embodiment, the guiding catheter is provided with a separate inner lumen which is configured to slidably receive the engaging device and which has a distal discharge port proximal to the distal end of the guiding catheter. In this embodiment there is no need for the guiding sheath.

The use of the system of the invention does not significantly occlude the inner lumen of the guiding catheter, so pressure measurements can be made and radiopaque liquid can be injected through the inner lumen of the guiding catheter while the guidewire or other guiding member is held in place. Additionally, the position of the guiding member is maintained independent of the guiding catheter.

The device of the invention has also been found suitable to retrieve items from within the patient's vasculature. The procedure is similar in most respects to the previously discussed methods. Generally the distal portion of the torqueable engaging member is positioned adjacent to the item to be retrieved. Rotation of the engaging member will cause its flexible distal extremity to wrap around the item within the patient's vasculature. The engaging member and the item are then withdrawn from the patient.

These and other advantages of the invention will become more apparent from the following detailed description of the invention and the accompanying exemplary drawings.

BRIEF DESCRIPTION OF THE DRAWINGS

FIG. 5 is an enlarged elevational view, partially in section, of the distal extremity of an alternative embodiment of the invention.

FIG. 6 is a transverse cross-sectional view of the embodiment shown in FIG. 5 taken along the lines 6—6 with the guidewire and catheter removed for purposes of clarity.

FIG. 7 is an elevational view of the distal extremity of the engaging member wrapped around a broken tip of a guidewire.

DETAILED DESCRIPTION OF THE INVENTION

Figure 1:
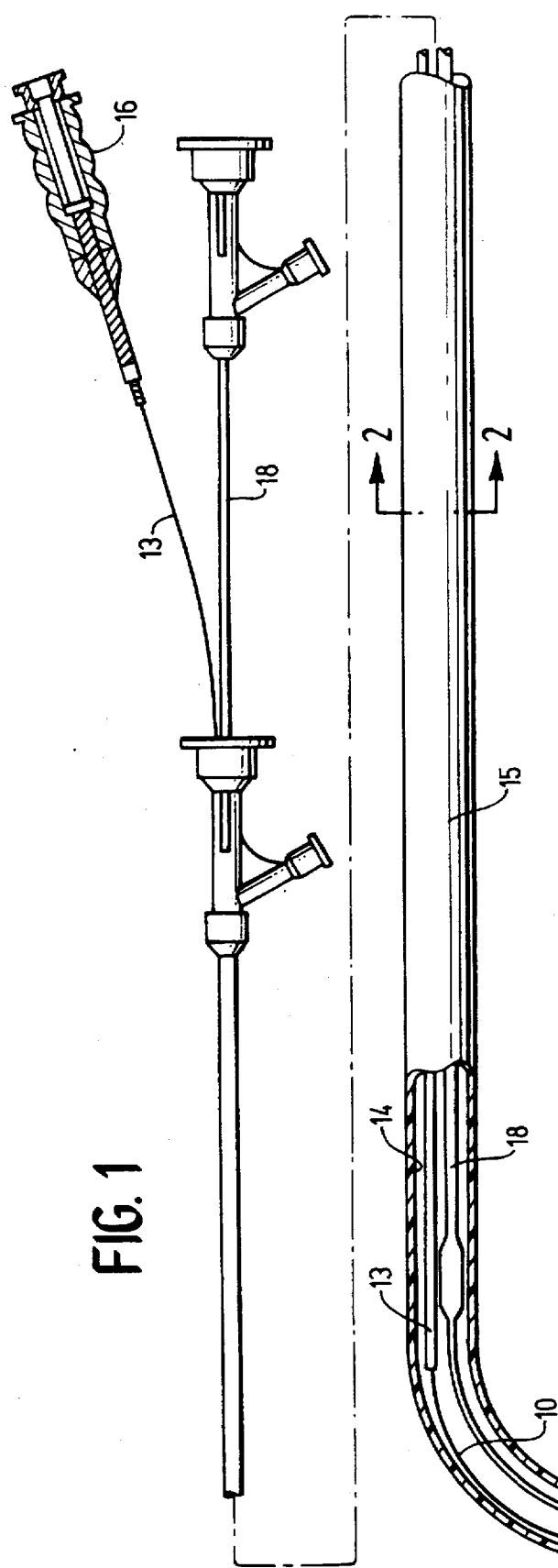
FIG. 1 is an elevational view, partially in section, of a catheter withdrawal system embodying features of the invention which is disposed within a guiding catheter.
Figure 2:
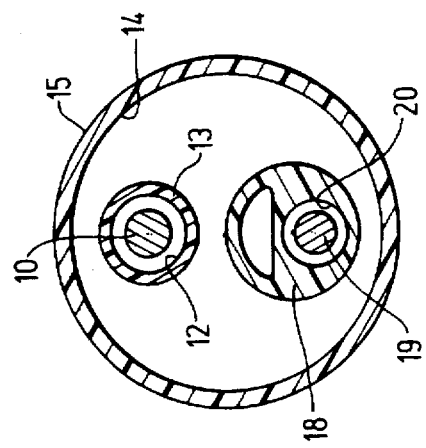
FIG. 2 is a transverse cross-sectional view of the system shown in FIG. 1 taken along the lines 2—2.
Figure 3:
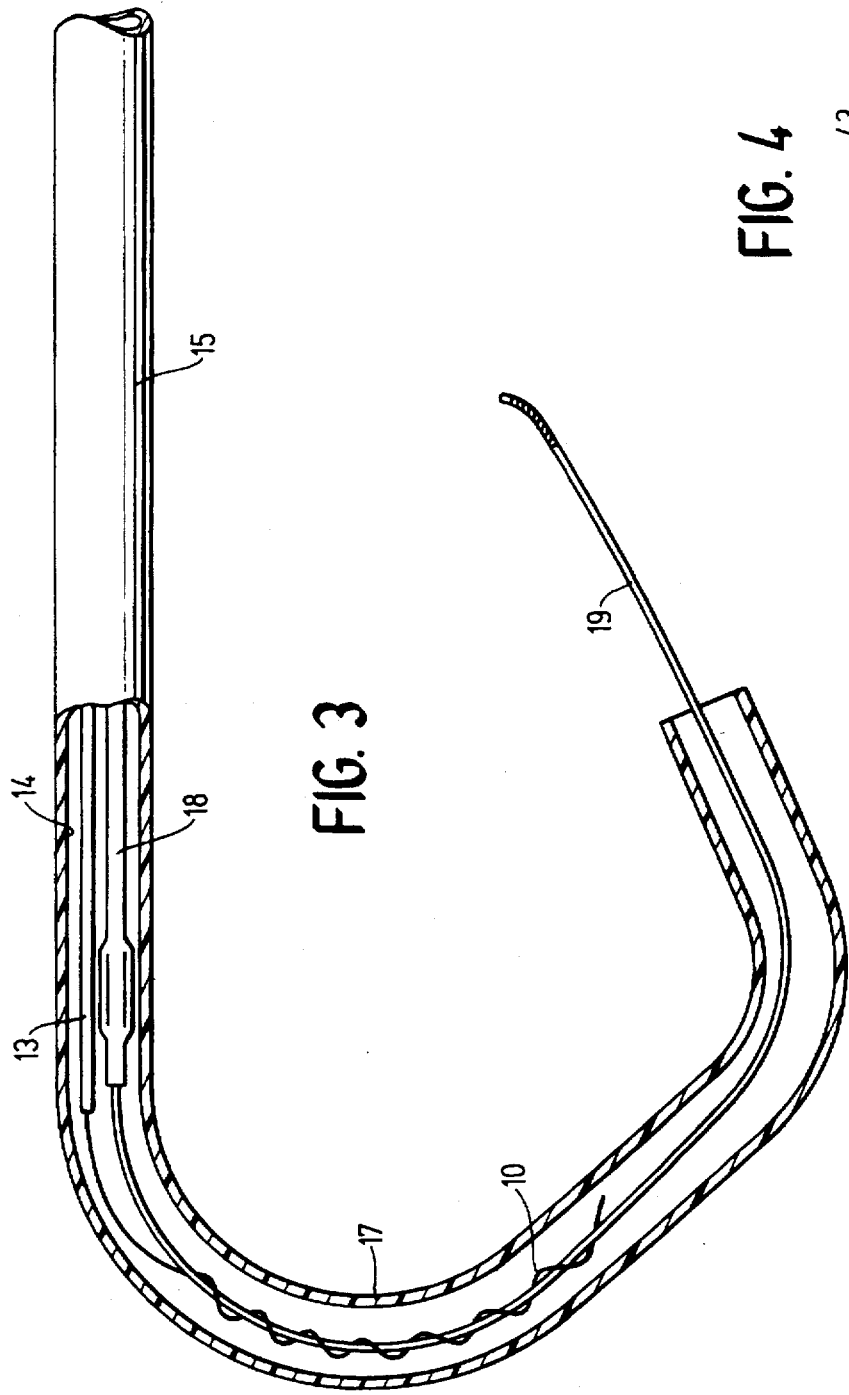
FIG. 3 is an enlarged view of the distal extremity of the system shown in FIG. 1 illustrating the distal extremity of the engaging device wrapped about an in-place guidewire.

With reference to FIGS. 1 and 2, the system of the invention includes an elongated engaging device 10 which has a shaped distal extremity 11 and which is slidably disposed within the inner lumen 12 of the guiding sheath 13. The guiding sheath 13 is slidably disposed within inner lumen 14 of guiding catheter 15. The proximal end of the engaging device 10 is provided with a knob or handle 16 for rotating and sliding the guidewire engaging device within the sheath 13. The distal tip 17 of the guiding catheter 15 is seated within an ostium of a patient's coronary artery. A conventional dilatation catheter 18 is disposed within the inner lumen 14 with an in-place guidewire 19 slidably disposed within the inner lumen 20 of the dilatation catheter 18 as shown in more detail in FIG. 2. The distal end of the dilatation catheter 18 is preferably disposed proximal to the distal end of the guiding sheath 12 so that the rotation of the engaging device 10 does not engage the dilatation catheter 18 in addition to the guidewire 19.

The system of the invention is typically utilized by positioning the dilatation catheter 18 so that the balloon thereof is disposed proximal to the distal tip 17 of the guiding catheter 15. The guiding sheath 13 is disposed within the inner lumen 14 of the guiding catheter 15 with the distal tip of the sheath being located proximal to the distal tip 17 of the guiding catheter 15 but distal to the distal end of the dilatation catheter 18. The engaging device 10 is advanced out the distal tip of sheath 13 into the distal tip 17 of the guiding catheter 15 by the handle 16 on the proximal end of engaging device 10 and is rotated by the handle 16 to wrap the flexible distal extremity 11 of the engaging device about the guidewire 19 and to engage the guidewire tightly enough to prevent significant movement of the guidewire when the dilatation catheter 18 is withdrawn from the patient or otherwise moved over the guidewire. The shaped distal extremity 11 of the engaging device 10 may be curved or angled to facilitate the wrapping thereof about the guidewire within the guiding catheter 15. About 3 to about 35 rotations, typically about 5 to about 20 rotations may be needed to wrap the distal extremity 11 about the guiding member securely enough to hold the distal portion of the guidewire 19 in position.

After the dilatation catheter 18 is removed from the guidewire 19, a replacement catheter (not shown) may then be mounted onto and advanced over the guidewire while the guidewire is held in place by the engaging device 10. To release or disengage the shaped distal extremity 11 of the engaging device 10, the engaging device is rotated in a direction opposite to the direction used to wrap the distal extremity 11 about the guidewire 19. The engaging device is withdrawn into the guiding sheath so that the engaging device and the guiding sheath 13 may be withdrawn from the patient.

An alternative method of use involves advancing the sheath 13 and the guidewire engaging device 10 beyond the distal end of the dilation catheter 18 but still within the guiding catheter 15, withdrawing the sheath 13 to expose the distal extremity 11 of the engaging device and then rotating the proximal extremity of the engaging device to wrap the distal extremity 11 about the guidewire 19 and tightly engage the guidewire to prevent movement thereof when an intravascular catheter is moved over the guidewire.

For coronary artery access through the patient's femoral artery, the length of the engaging device is about 80 to about 120 cm. and the diameter of the engaging device may be about 0.004 to about 0.014 inch (0.1–0.36 mm). If desired, the proximal portion of the engaging device 10 may be of larger diameter and a different composition, e.g. stainless steel, with the distal section being formed of superelastic NiTi alloy with a suitable tubular connection such as described in copending application Ser. No. 07/994,679 filed on Dec. 22, 1992, which has been incorporated herein by reference.

The guidewire engaging device 10 is preferably made from a superelastic NiTi alloy such as described in copending application Ser. No. 08/071,322, filed Jun. 2, 1993, which is incorporated herein. As indicted therein the NiTi alloy consists essentially of about 30 to about 52% (atomic) titanium (about 46% by weight) and the balance nickel and up to about 10% (atomic) of one or more additional alloying elements selected from the group consisting of up to 3% (atomic) each of iron, cobalt, chromium, platinum and palladium and up to about 10% (atomic) copper and vanadium. Generally, the nickel level should be at least about 38% (atomic) but at nickel levels above 52% (atomic) the alloy becomes too brittle to fabricate by cold working. A typical composition is about 55.9% (wt) Ni and 44.1% (wt) Ti. As used herein all references to percent alloy compositions are atomic percent unless otherwise noted. The superelastic alloy has a austenite phase which is stable at or below body temperature and which will transform to a lower modulus martensite phase upon the application of stress. The rate of change of stress during the phase transformation is much less than the rate of change of stress either before or after the stress-induced transformation. In some instances the stress level during the phase change is almost constant.

To form the elongated superelastic portion of the guiding member, elongated solid rod or tubular stock of the preferred alloy material is first thermomechanically processed through a series of cold working and inter-annealing at temperatures between about 600° to about 800° C. for about 5 to about 30 minutes and then given a final cold working, preferably by drawing, to effect a final size reduction of about 10% up to about 75% in the transverse cross section thereof, preferably about 30 to about 70%. After the final cold working, the material is given a heat treatment at a temperature of about 280° to about 600° C. for about 0.5 to about 60 minutes to generate the superelastic properties. To impart a straight memory, the cold worked material may be subjected to a longitudinal stress equal to about 5% to about 50%, preferably about 10% to about 30%, of the yield stress of the material (as measured at room temperature) during the heat treatment. This thermomechanical processing imparts a relatively uniform residual stress in the material. Another method involves mechanically straightening the wire after the cold work and then heat treating the wire at temperatures between about 280° to about 600° C., preferably about 450° to about 525° C. As in the previous heat treatment, a longitudinal stress equal to about 5% to about 50% of the room temperature yield stress is applied during heat treatment. The latter combined treatment provides substantially improved one-to-one torque response, i.e. it is substantially whip free, which greatly facilitates the wrapping of the distal portion about the guidewire. The cold worked and heat treated alloy material which has been treated as above has an austenite finish transformation temperature $A_f$ of about –20° to about 40° C. and usually less than body temperature. To obtain more consistent final properties, it is preferred to fully anneal the rod prior to cold working so that the NiTi alloy material will always have the same metallurgical structure at the start of the cold working to provide consistent final properties and to ensure adequate ductility for cold working. It will be appreciated by those skilled in the art that the alloy can be cold worked in a variety of ways other than drawing, such as rolling or swaging. The resultant superelastic wire will exhibit stress induced transformation from austenite to martensite at a relatively constant stress level above 70 ksi (483 MPa), usually above 90 ksi (621 MPa). As a result the guidewire engaging device formed of this material is very flexible, it can be readily advanced through a guiding sheath disposed within a guiding catheter, it will effectively transmit the torque applied thereto without causing the guiding member to whip and the distal extremity thereof will easily wrap around and tightly secure a guidewire within a guiding catheter.

The guiding sheath 13 may be formed of a variety of metal or plastic material and generally will be shorter than the guidewire engagement member 10, e.g. about 4 to about 10 cm shorter and typically about 6 cm shorter. The sheath is short enough to expose the distal extremity 11 of the engaging device 10 which wraps around the guidewire and to allow a portion of the engaging device to extend out the proximal end guiding sheath 13. The diameter of the inner lumen 12 of the guiding sheath 13 is sufficiently large to slidably receive the engaging device 10 and will generally be at least about 0.001 inch (0.025 mm), preferably at least 0.002 inch (0.051 mm) larger than the OD of the portion of the engaging device which will be disposed within the inner lumen. The guiding catheter 15, the dilatation catheter 18 and the guidewire 19 may be formed of conventional material and may be of convention construction and materials. The guidewire may be as described in the above identified co-pending application Ser. No. 07/994,679 wherein a tubular superelastic NiTi alloy member connects a distal portion formed of a superelastic NiTi alloy with a stainless steel proximal portion.

Figure 4:
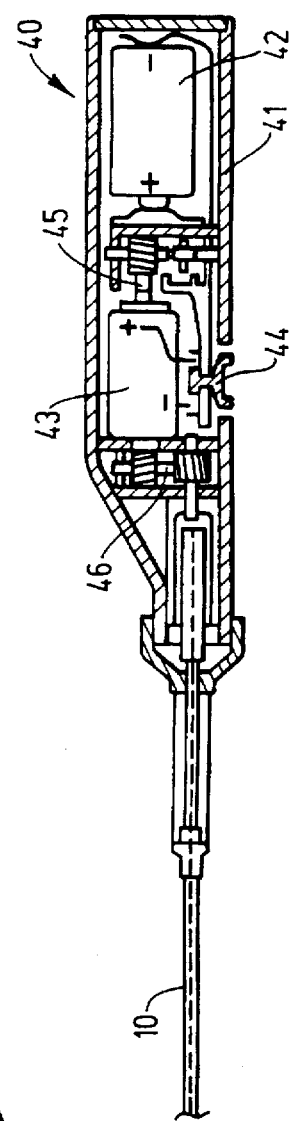
FIG. 4 is a schematic elevational view, partially in section, of an electrical torquing device for rotating the engaging device.

FIG. 4 illustrates a torquing device 40 for rotating the engaging device 10 which is secured to the proximal end thereof which includes a housing 41, a battery 42, an electrical motor 43, and an operating switch 44. The battery 42 is electrically connected to the motor 43 by means of the switch 44 and the polarity switching assembly 45. The rotation of the motor 43 is transferred to the proximal end of the engaging device 10 by means of the gear assembly 46. Movement of the operating switch 44 toward the proximal end of the engaging device 10 causes the rotation of the motor 43 and thus the engaging device in a first direction and movement of the operating switch 44 away from the engaging device reverses the direction of the rotation. The motor 43 is operated in a first direction to cause the rotation of the shaped distal extremity 11 of the engaging device 10 to engage the distal portion of a guiding member and then the rotational movement of the motor 44 is reversed to disengage the shaped distal extremity from the guiding member. The torquing device 40 is urged forwardly when the engaging device is engaging the guiding member and pulled backwardly when the engaging device is disengaging from the guiding member. The operation of the torquing device to cause the engagement with the guiding member is usually continued until the rotation of motor 43 slows or ceases, which indicates that a secure engagement has been made. A slight pull on the torquing device 40 when rotating the drive to disengage the shaped distal extremity of the engaging device will clearly indicate to the physician when the disengagement is complete.

FIGS. 5 and 6 illustrate an alternative embodiment of the invention in which a guiding catheter 50 is provided with a first inner lumen 51 configured for slidably receiving a guidewire 52 and catheter 53 and with a second inner lumen 54 which is configured to slidably receive the engaging member 55. The first inner lumen 51 extends from the proximal end of the guiding catheter 50 to its distal end. The second inner lumen 54 extends from the proximal end to a discharge port 56 spaced proximally from the distal end of the guiding catheter 50 a sufficient distance, e.g. about 2 to about 10 cm. to allow the flexible distal portion of the engaging member to wrap around and engage the guidewire 52 as shown. The In this embodiment, the second inner lumen 54 takes the place of the guiding sheath in the previously discussed embodiment.

FIG. 7 illustrates the grasping of an item 60 which in this case is a broken distal tip of a guidewire within the patient's vasculature. The engaging member 62 is rotated from its proximal extremity which extends out of the patient by means of a driving unit as shown in FIG. 4 to cause the distal extremity 62 to wrap around the item 60 so that both can be withdrawn. A variety of other means may be employed on the distal extremity of the engaging member to engage or grasp the item so that it can be withdrawn from the patient's blood vessel.

While the invention has been described herein in terms of certain preferred embodiments directed to the exchange of an over-the-wire balloon dilatation catheters, those skilled in the art will also recognize that the invention can be used with a wide variety of balloon dilatation catheters, including rapid exchange type dilatation catheters, atherectomy catheters and other intravascular catheters which are advanced through a patient's vasculature. Various modifications can been made to the invention. For example, the engaging device may have forcep-type jaws or other types of grasping means operable from the proximal end thereof to releaseably engage the guiding member independent of the guiding catheter so as to maintain the position of the guidewire. Additionally, the forgoing means need not be a motor-driven unit, but may be a manually-rotatable mechanism or any other means to apply a torque to the proximal end of the engaging device. Other improvements and modifications may be made to the invention without departing from the scope thereof.

What is claimed is:

1. A guiding catheter having an elongated shaft with proximal and distal ends, a distal portion shaped to facilitate entry into a patient's coronary ostium, a first inner lumen extending from the proximal end to the distal end configured to slidably receive a catheter and guidewire and a second inner lumen extending from the proximal end to a discharge port at a location spaced proximally from the distal end and configured to slidably receive an elongated torqueable engaging device which has a flexible distal portion configured to extend out the discharge port and wrap around and rotatively engage a distal portion of a guidewire disposed within the first inner lumen between the distal end of the guiding catheter and the discharge port.

2. A method for retrieving an item from within a patient's vasculature, comprising:

a) providing an elongated engaging device with proximal and distal ends and a rotatable engaging means on a distal portion thereof;

b) advancing the elongated engaging device within the patient's vasculature until the engaging means is adjacent to a portion of the item for retrieval;

c) operating the rotatable engaging means from the proximal end of the elongated engaging device to rotatively engage the item for retrieval; and d) withdrawing the engaging device and retrieved item engaged by the rotatable engaging means of the engaging member to remove the retrieved item from the patient's vasculature.

3. The method of claim 2 wherein the engaging means is a flexible distal portion which is wrapped about the item.

4. The method of claim 3 wherein the flexible distal portion of the elongated engaging device is rotated from its proximal end to wrap the flexible distal portion thereof about the item to be retrieved.

* * * * *